United States Patent [19]

Boyington

[11] Patent Number: 4,585,119
[45] Date of Patent: Apr. 29, 1986

[54] TOOTHBRUSH SANITIZER DEVICES

[76] Inventor: Richard Boyington, 386 13th Ave., Vero Beach, Fla. 32960

[21] Appl. No.: 690,108

[22] Filed: Jan. 9, 1985

[51] Int. Cl.⁴ .............................................. B65D 85/20
[52] U.S. Cl. ................................. 206/209.1; 206/209; 206/362.3; 211/74
[58] Field of Search ..................... 206/209, 209.1, 205, 206/362, 362.1, 362.3; 211/71, 74; 248/128, 146, 154

[56] References Cited

U.S. PATENT DOCUMENTS

| | | | |
|---|---|---|---|
| 1,278,789 | 9/1918 | Thompson | 206/209.1 |
| 1,588,781 | 6/1926 | Stoddard | 206/362.3 |
| 1,716,842 | 6/1929 | Sulak | 206/362.3 |
| 1,987,472 | 1/1935 | Feldon | 206/209.1 |
| 2,881,947 | 4/1959 | Hancock | 211/71 |
| 3,039,616 | 6/1962 | Proffit | 211/74 |
| 3,175,695 | 3/1965 | Goodman et al. | 211/74 |
| 3,461,728 | 8/1969 | Paoli | 211/74 |
| 4,124,122 | 11/1978 | Emmitt | 211/74 |

Primary Examiner—George E. Lowrance
Assistant Examiner—Jimmy G. Foster
Attorney, Agent, or Firm—Carroll F. Palmer

[57] ABSTRACT

Devices that serve to sanitize and clean toothbrushes while storing them between brushing use comprise an elongated, tubular container having a necked-down section positioned between its lower, closed end and the upper, open end. The lumen of the container is larger than the width of the bristled portion of toothbrushes while the lumen of the necked-down section is slightly less than such width so that bristles of a toothbrush are flexed when it is inserted into or withdrawn from the container.

Holders for the containers together with flexible retainers that cooperate with the necked-down section lock the containers in the holders and there are cover elements to close the open ends of the containers when toothbrushes are stored therein.

6 Claims, 9 Drawing Figures

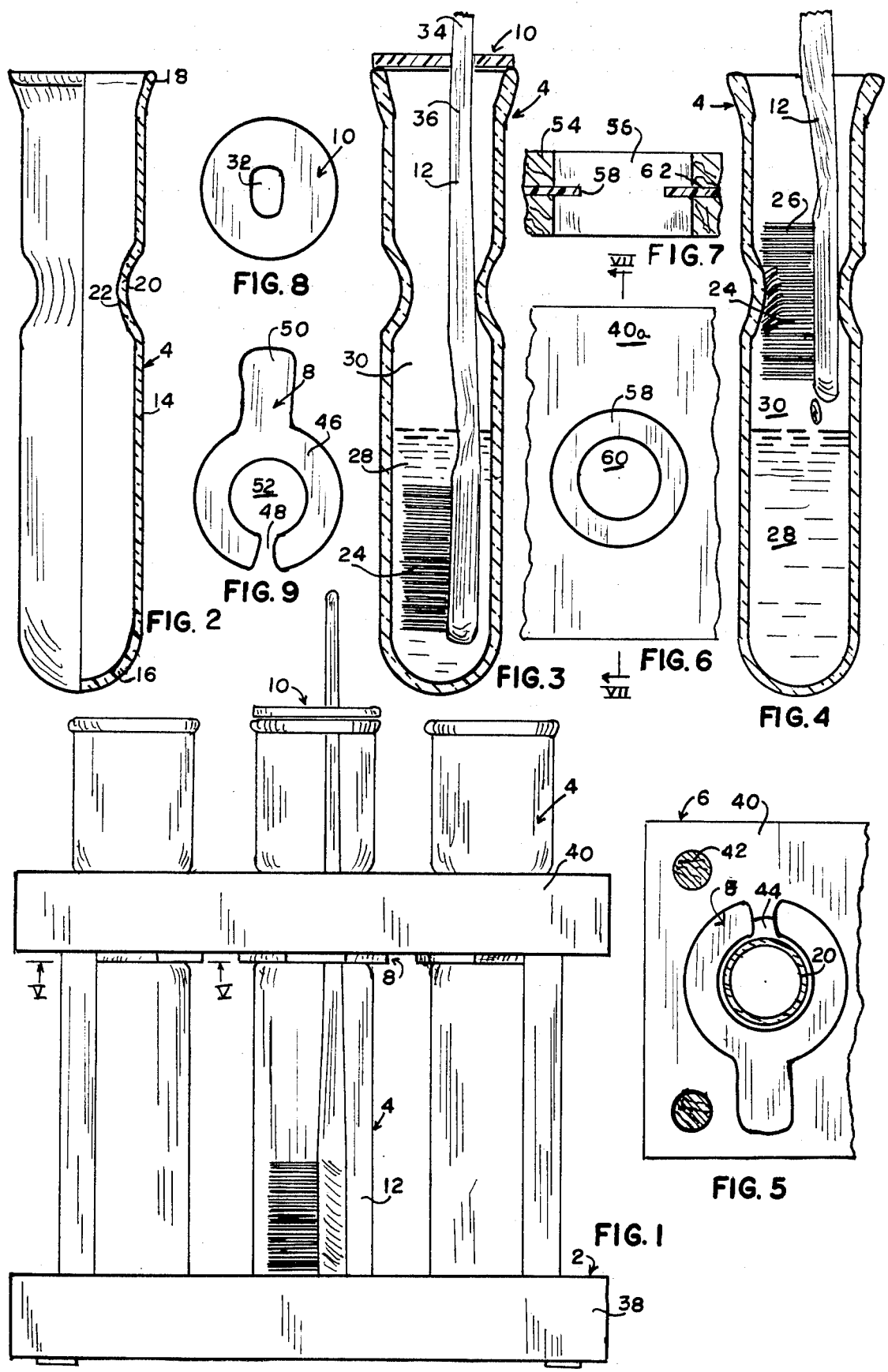

TOOTHBRUSH SANITIZER DEVICES

BACKGROUND OF THE INVENTION

1. Field of the Invention

This invention relates broadly to devices for sanitizing toothbrushes when not in use. More particularly, it concerns holders for toothbrushes that serve to sanitize them during storage and clean their bristles during insertion or removal from the devices.

2. Description of the Prior Art

Toothbrushes are conventionally returned to holders, racks, etc. after use by their owners in wet condition and containing bacteria, possible food particles, etc. that may have been transferred thereto from the mouth of the owner during the use. It is also customary for the a toothbrush so stored to be uncovered and exposed to ambient. Consequently, toothbrushes stored in this manner promote bacteria or mold growth and are exposed to insects or anything else that might come in contact with them while the owner is not there to observe. In other words, toothbrushes are conventionally held and stored when not in use under relatively unsanitary conditions.

The unsanitary storage problem has not gone unnoticed and there have been devised in the past a variety of storage devices, holders, etc. that attempt to cope with it. Representative of such prior art endeavors are the disclosures in the following U.S. Pat. Nos.: 942,058, 1,079,618, 1,050,864, 1,424,434, 1,061,978, 1,480,814, 1,062,961, 1,588,781, 1,070,858, 1,713,379.

In spite of the extensive amount of work devoted to the indicated toothbrush storage problem reflected by the listed prior art and much more, the unsanitary storage mentioned above remains as the norm. This suggests that the prior art attempts at solutions have been defective in some way or unacceptable to toothbrush users for one reason or other.

OBJECTS

A principal object of this invention is the provision of new improvements in devices for storing toothbrushes when not in use while, at the same time, cleaning their bristles and sanitizing them.

Further objects include the provision of:

1. Toothbrush storage devices designed to shake loose any foreign particles from their bristles in the course of their storage in the devices.

2. Such devices that serve to keep the stored brushes free of insects, dust, hair, hair-sprays that would otherwise contact the brushes if stored with their bristles exposed to ambient.

3. Such devices that may be conveniently located in a bathroom or other point of use of a toothbrush by its owner.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become aapparent to those skilled in the art from this detailed description.

SUMMARY OF THE INVENTION

The objects are accomplished in accordance with the invention by the provision of devices to sanitize and clean toothbrushes while storing them between brushing use comprising an elongated, tubular container having a necked-down section positioned between its lower, closed end and the upper, open end. The lumen of the container is larger than the width of the bristled portion of toothbrushes to be stored therein while the lumen of the necked-down section is slightly less than the width so that bristles of a toothbrush are flexed and squeezed when it is inserted into or withdrawn from the container.

A holder for the container is provided having a transverse bore therein slightly larger in diameter than the OD of the container, and also there is retainer means that utilizes the necked-down sections of the containers to lock them in the holder.

In preferred embodiments, the retainer means is a flexible ring member having central hole therein having a diameter less than the OD of said container and greater than the OD of said necked-down section, e.g., a ring member comprises a ring of plastic material, an integral, lateral tab handle and a slot in said ring opposed to said handle.

The holder may comprise a shelf containing said transverse bore and, in addition, a base and uprights fixing the shelf apart and parallel to the base.

Cover elements to close the open end of the containers when toothbrushes are stored therein may include a plastic disc that fits snugly over the end of a toothbrush held in the container of the new devices.

BRIEF DESCRIPTION OF THE DRAWINGS

A more complete understanding of the invention may be obtained by reference to the accompanying drawings wherein:

FIG. 1 is a lateral view of an embodiment of the devices of the invention comprising three separate toothbrush containers.

FIG. 2 is a lateral view, one-half in section, of a single toothbrush container of the invention.

FIG. 3 is a sectional view of a single toothbrush container of the invention shown holding a toothbrush in normal storage position.

FIG. 4 is a sectional view of a single toothbrush container of the invention shown as a toothbrush is being withdrawn for the normal storage position.

FIG. 5 is a fragmentary, sectional view taken on the line V—V of FIG. 1.

FIG. 6 is a fragmentary, plan view of a second embodiment of a container holder of the invention.

FIG. 7 is a fragmentary, sectional view taken on the line VII—VII of FIG. 6.

FIG. 8 is a plan view of a container cover of the invention.

FIG. 9 is a plan view of a container retension member of the invention.

DESCRIPTION OF THE PREFERRED EMBODIMENTS

Referring in detail to the drawings, the toothbrush sanitizer device 2 of the invention basically comprises a plurality of containers 4, a holder 6, a plurality of retainers 8 and container covers 10. One of the containers 4 is shown storing a toothbrush 12.

Each container 4 comprises an elongated tube 14 closed at the bottom end 16 and open at the top end 18.

An essential element of the new devices is a necked-down portion formed in the container 4, preferably located so that its position 22 of smallest lumen is between about 0.5 to 0.7 times the distance between the top and bottom edges of the container 4. By reference to FIGS. 3 and 4, it will be seen that the lumen of the container, e.g., the lumen above and below the necked-down portion 20, is larger than the width of the bristled portion 24 of the toothbrush 12 while the smaller lumen at position 22 is slightly less so that bristles 26 of the toothbrush are gently flexed when the brush is inserted into or withdrawn from the container 4. As a result, as the brush 12 is withdrawn, antiseptic or like solution 28 held in container 4 in which the brush 12 is immersed during normal storage (FIG. 3) will be squeezed from the brush bristles 26 by the flexing action of the container portion 20. Such flexing action in conjunction with the wetted condition of the bristles 26 serves to dislodge any food or other particles that may be adherent to the bristles 26.

Advantageously, the container 4 is a vial made of glass, but it can be made of any other suitable nonabsorbent material, e.g., plastic, rubber, ceramic, etc. Typically, the vials are approximately 13 cm. high (10 cm. for childrens brushes) and 2.5 cm. in diameter with a neck-down portion lumen of about 1.5 cm. at about ⅓ of the way down the vial. Preferably, the top of the vial is slightly flared, i.e., trumpet shaped, which makes for ease of insertion of toothbrushes. The volume of the vial from the flared top to the necked-down portion 20 serves to retain any spray from the brush bristles inside the vial as the brush bristles 26 pass through the restricted lumen at position 22.

The tapered neck portion 20 bends the bristles 26 together as the toothbrush 12 is pushed or pulled through. As it passes the neck 20 and into the reservoir portion 30, the bristles 26 snap back into shape to shake loose any foreign particles from the bristles 26. The brush 12 is then submerged in the reservoir 30 holding the liquid 28 so that the brush 12 is soaked clean and sanitized.

When the toothbrush 12 is in the container 4, the upper level of the liquid 28 should be no higher than the neck 20. When the brush is removed from the reservoir 30 and passes through the neck 20, it receives the same cleaning action as when it is inserted. Nevertheless, the brush 12 should be rinsed before insertion and after removal from the container 4.

The cover 10 serves to keep dust, etc. from entering the container 4 during storage. Advantageously, the cover 10 is a disc of plastic with a central opening 34 that is sized to fit snugly over the upper section 34 of the handle 36 of the brush 12. Other forms of covers made of various material may be used, e.g., it may have a depending skirt (not shown).

A preferred type of holder 6 for the containers 4 comprises a base 38, shelf 40 and uprights 42. The shelf 40 contains bores 44 of diameter slightly larger than the OD of the vials 4. Similar bores (not shown) are located in the base 38 beneath corresponding bores 44 in the shelf 40 so the bottoms 16 of the vials rest in the base 38.

The vials 4 are secured in the holder 6 by flexible retainers 8 that cooperate with the neck portions 20 of the vials to lock then in the holder 6. A preferred form of retainer 8 (see FIG. 9) comprises a flat plastic member comprising a ring portion 46 with a slot 48 therein opposite to the handle tab 50. The opening 52 in the retainer ring 46 fits around the neck portion 20 (see FIG. 5) of the container 4 to effectively clamp the container 4 in the holder 6. By pulling on the tab 50, the retainer 8 may be removed from around the neck 20 of the container 4 to allow it to be easily removed from the holder 6, such as for cleansing, etc.

The holder 6 is illustrated as made of wood, but they can be made of plastic, ceramic, glass, etc. Of course, the relative position of the base 38 and shelf 40 is fixed so that the retainers 8 may function in conjunction with the bottom of the shelf 40 and the vial necks 20 as described to lock the containers 4 in the holder 6.

Other forms of holders and retainers for the new containers can be provided as illustrated, in part, by FIGS. 6 & 7. In this embodiment, the shelf 54 comprises a bore 56 sized to admit a container 4 and a flexible ring member 58 having a central hole 60 is fixed in a groove 62 in the shelf 54. The hole 60 is slightly larger than the OD of the neck 20 of a container 4 so that the container can be forced into the member 58 until the neck 20 of the container enters the hole 60. When so positioned the container is securely held in the shelf 54. Such shelves can be part of a holder such as holder 6 or they may be per se mounted by brackets or the like directly to a bathroom wall, cabinet, etc.

The new devices of the invention provide users of toothbrushes with improved means to sanitize the brushes while being stored. At the same time, the brushes are kept free of insects, dust, hair, spray aerosols, etc. Moreover, these devices are as easy to employ for brush storage as the conventional holders or racks that leave brushes fully exposed to ambient and provide no sanitizing during storage.

The embodiments of the invention in which an exclusive property or privilege is claimed are defined as follows:

1. A device to sanitize and clean toothbrushes while storing them between brushing use comprising:
    an elongated, tubular container having a necked-down section positioned between its lower, closed end and the upper, open end,
    the lumen of said container being larger than the width of the bristled portion of toothbrushes to be stored therein while the lumen of said necked-down section is slightly less than said width so that bristles of a toothbrush are gently flexed when it is inserted into or withdrawn from said container,
    a holder for said container having a transverse bore therein slightly larger in diameter than the OD of said container, and
    retainer means that utilizes said necked-down section to enable said container to be locked in said holder including:
        a ring of plastic material having an OD larger than said bore,
        an integral, lateral tab handle and a slot in said ring opposed to said handle.

2. The device of claim 1 having a cover element to close the open end of said containers when a toothbrush is stored therein.

3. The device of claim 1 wherein said holder comprises a shelf containing said transverse bore.

4. The device of claim 3 wherein said holder comprises a base and uprights fixing said shelf apart and parallel to said base.

5. A device to sanitize and clean toothbrushes while storing them between brushing use comprising:
    an elongated, tubular container having a necked-down section positioned between its lower, closed end and the upper, open end, the lumen of said container being larger than the width of the bristled portion of toothbrushes to be stored therein while the lumen of said necked-down section is slightly less than said width so that bristles of a toothbrush are gently flexed when it is inserted into or withdrawn from said container, a holder for said container having a shelf containing a transverse bore therein slightly larger in diameter than the OD of said container, retainer means that utilizes said necked-down section to lock said container in said holder comprising a flexible ring member having central hole therein having a diameter less than the OD of said container and greater than the OD of said necked-down section, said ring member being fixed to said shelf concentric with said bore.

6. The device of claim 5 wherein said holder comprises a base and uprights fixing said shelf apart and parallel to said base.

* * * * *